United States Patent [19]

Paxson

[11] 4,409,397
[45] Oct. 11, 1983

[54] ASYMMETRIC HYDROGENATION OF TETRA-SUBSTITUTED OLEFINIC ACIDS AND DERIVATIVES

[75] Inventor: Timm E. Paxson, Houston, Tex.

[73] Assignee: Shell Oil Company, Houston, Tex.

[21] Appl. No.: 375,437

[22] Filed: May 6, 1982

[51] Int. Cl.³ .................... C07C 59/48; C07C 53/194
[52] U.S. Cl. ................................. 562/496; 562/468; 562/491; 560/55; 560/57; 564/170
[58] Field of Search .......................... 562/496

[56] References Cited

U.S. PATENT DOCUMENTS 3,849,480 11/1974 Knowles .............................. 260/490
4,119,652 10/1978 Knowles .............................. 260/429
4,194,051 3/1980 Bachman et al. ..................... 560/60

OTHER PUBLICATIONS

Merrill, R. E. "Asymmetric Synthesis Using Chiral Phosphine Ligands", Reaction Design Corporation, pp. 11–12 (1979).

Primary Examiner—Paul J. Killos

[57] ABSTRACT

Tetra-substituted olefinic acids and derivatives of the formula

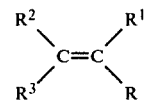

wherein R is —COOM in which M is a cation forming a soluble salt or —COOR⁴ or —CON(R⁴)₂ in which each $R^4$ is independently a hydrogen atom or an alkyl group; $R^1$ is an optionally substituted alkyl, cycloalkyl, aryl or heterocyclic group; and $R^2$ or $R^3$ each independently is an optionally substituted alkyl or cycloalkyl group or $R^2$ and $R^3$ together with the carbon atom to which they are attached form a carbocyclic ring, are asymmetrically hydrogenated in the presence of a coordinated complex of rhodium, iridium, or ruthenium in combination with a chiral metallocenylphosphine or pyrrolidinylphosphine ligand.

24 Claims, No Drawings

ASYMMETRIC HYDROGENATION OF TETRA-SUBSTITUTED OLEFINIC ACIDS AND DERIVATIVES

BACKGROUND OF THE INVENTION

1. Field of the Invention

The present invention relates to a process for the asymmetric hydrogenation of tetra-substituted olefinic acids and derivatives thereof.

2. Description of the Prior Art

Many chemicals, particularly those having biological applications, are desirable to have in a stereochemically pure form. Quite often chemicals are prepared in a racemic form followed by optical resolution. It would be more economical and efficient to obtain the desired stereochemical form and the exclusion of the undesired stereoisomeric form(s) at an early stage of synthesis through the stereoselective creation of chiral centers.

There is a substantial amount of literature and patents on a variety of asymmetric reactions, including hydrogenation. For example, U.S. Pat. No. 3,849,480 describes the asymmetric hydrogenation of olefins with certain coordination complex catalysts. Many asymmetric hydrogenation reactions involve the treatment of ketones or highly hindered olefins. Achiwa, *Fundam. Res. Homogeneous Catal.*, pages 549–64 (1979) discloses the asymmetric hydrogenation of amino- or acylamino olefnic compounds, such as L-beta-methylaspartic acid. However, Cullen et al., *J. Amer. Chem. Soc.*, 102 (3), pages 988–993 states that substrates without acylamino groups are not hydrogenated by catalysts such as ferrocenylphosphine-rhodium complex catalysts. By contrast, Applicant has found that certain chiral phosphine catalyst are useful for asymmetric hydrogenation of certain highly hindered olefins, which are tetra-substituted olefinic acids and certain derivatives thereof and which do not contain the nitrogen atom one atom removed from the olefinic carbons as taught in the art.

SUMMARY OF THE INVENTION

The present invention is directed to a process for the asymmetric hydrogenation of a tetra-substituted olefinic acid or derivative thereof, which comprises the hydrogenation of a tetra-substituted olefinic acid or derivative thereof having the formula I

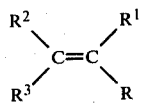

wherein R is —COOM in which M is a cation forming a soluble salt or —COOR$^4$ or —CON(R$^4$)$_2$ in which each R$^4$ is independently a hydrogen atom or an alkyl group; R$^1$ is an optionally-substituted alkyl, cycloalkyl, aryl or heterocyclic group; and R$^2$ and R$^3$ each independently is an optionally-substituted alkyl or cycloalkyl group or R$^2$ and R$^3$ together with the carbon atom to which they are attached form a carbocyclic ring, in the presence of a coordination complex of rhodium, ruthenium or iridium in combination with a chiral metallocenylphosphine selected from a ferrocenyl-, a ruthenocenyl- or a osmocenylphosphine ligand or pyrrolidinylphosphine ligand.

Thus, the olefinic acids and derivatives thereof of formula I (also called the substrate) are tetra-substituted to the two olefinic carbon atoms in each of the four possible positions and one of the olefinic carbon atoms bears substituents that are both hydrocarbyl and non-aromatic in character. In the asymmetric hydrogenation process of the invention, these compounds of formula I are hydrogenated at their prochiral carbon-to-carbon double bond in such a way as to produce an excess of one enantiomer of the resulting saturated product. The term "prochiral" used herein refers to a double-bonded carbon atom center having three unlike substituents, e.g. X=CYZ, such that the introduction of a fourth substituent leads to a chiral carbon atom center, e.g. X-CAYZ.

A "Chiral phosphine" as used in this invention denotes either a phosphine compound comprised of phosphorus having substituted thereon three hydrocarbon radicals which are not all identical or a phosphine compound which has three hydrocarbon radical substituents at least one of which is chiral.

"Enantiomer excess" as used in this invention refers to a numerical value expressed as percent of the predominance of one enantiomer in relation to another, i.e., the excess of the S-enantiomer expressed as a percent of the S-enantiomer minus the percent of R-enantiomer.

The terms "R-enantiomer" and "S-enantiomer" refer to the absolute configuration of the substituents about an asymmetric carbon atom in optically active organic compounds as prescribed in standard nomenclature.

Some more specific examples of the substituents on the tetra-substituted olefinic acids and derivatives thereof of formula I are when R is —COOH, —COOR$^4$, —CONH$_2$, —CONHR$^4$, —CONR$_2^4$ in which R$^4$ is an alkyl group containing from 1 to 10 carbon atoms or —COOM in which M is a cation forming a soluble salt and selected from an alkali metal, alkaline earth metal, amine or quaternary ammonium cation; R$^1$ is an alkyl group containing from 1 to 16 carbon atoms, a cycloalkyl group containing from 3 to 7 ring carbon atoms, optionally substituted by one or more alkyl groups, an aryl group containing from 6 to 10 ring carbon atoms optionally ring substituted by one or more halogen atoms, alkyl, alkoxy, haloalkyl, haloalkoxy, alkylthio, haloalkylthio groups, a methylenedioxy group, an aralkyl group containing from 7 to 11 carbon atoms optionally substituted by one or more halogen atoms or alkyl groups, or a heterocyclic group showing aromatic characteristics and containing 5 or 6 ring atoms at least one of which is oxygen, nitrogen or sulfur; R$^2$ and R$^3$ each independently is an alkyl group containing from 1 to 10 carbon atoms or a cycloalkyl group containing from 3 to 7 ring carbon atoms optionally substituted by one or more alkyl groups or R$^2$ and R$^3$ together with the carbon atoms to which they are attached form a carbocyclic ring containing from 3 to 12 ring carbon atoms. For example, R is —COOH, —COOCH$_3$, —COOC$_{10}$H$_{19}$, —CONH$_2$, —CONHCH$_3$, —CON(C$_3$H$_7$)$_2$, —COOCa, —COO$^-$N(CH$_3$)$_4{}^+$ and the like; R$^1$ is methyl, ethyl, n-propyl, isopropyl, n-butyl, isobutyl, isoamyl, n-hexyl, n-octyl, n-decyl, 2-chloroethyl, cyclopropyl, cyclohexyl, phenyl, naphthyl, p-chlorophenyl, p-(difluoromethoxy)phenyl, p-methylphenyl, m-methoxyphenyl, benzyl, phenethyl, 2,3-dimethybenzyl, p-chlorobenzyl, pyridinyl, pyrimidinyl, pyrazinyl, thienyl, pyrrolyl, furanyl and the like; R$^2$ and R$^3$ each independently is methyl, ethyl, n-propyl, isopropyl, isobutyl, sec-butyl, n-decyl, ethyl, cyclopropyl, cyclohexyl or R$^2$ and R$^3$ are taken together with the carbon atom to which they are attached are cyclopropyl, cyclobutyl, cyclohexyl or cyclododecyl and the like.

In the above groups, optional substituents mentioned are meant to include halogen atoms having an atomic number of 9 or 17, or alkyl, alkoxy, haloalkyl, haloalkoxy, alkylthio, haloalkylthio in which each alkyl portion contains from 1 to 4 carbon atoms and each halogen atom is an atomic number of from 9 to 17.

The process of the invention is especially suitable when the tetra-substituted olefinic acid or derivative thereof is one in which $R^1$ is an alkyl group containing from 1 to 6 carbon atoms, a phenyl group optionally substituted by a halogen atom, or an alkyl, haloalkyl, alkoxy or haloalkoxy group, or a naphthyl group; $R^2$ and $R^3$ each independently is an alkyl group containing from 1 to 6 carbon atoms or a cycloalkyl group containing from 3 to 6 ring carbon atoms or $R^2$ and $R^3$ together with the carbon atom to which they are attached is a cycloalkyl group containing 3 to 4 ring carbon atoms.

Because of the biological properties of their ultimate pyrethroid ester products, it is particularly desirable to use the process of the present invention to hydrogenate tetra-substituted olefinic acids of the formula II below

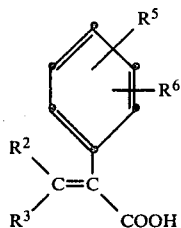

II wherein $R^2$ and $R^3$ each is a methyl group or when taken together with the carbon atom to which they are attached form a cyclopropyl group; $R^5$ and $R^6$ each independently is hydrogen, chlorine, fluorine, bromine, or an alkyl or alkoxy group each optionally substituted by one or more halogen atoms. For example, the process is applicable to olefinic acids of the above formula II wherein $R^5$ is hydrogen, chlorine, fluorine, bromine or an alkyl or alkoxy group optionally substituted by one or more chlorine or fluorine atoms and $R^6$ is hydrogen or chlorine. Preferably $R^2$ and $R^3$ each is methyl, $R^5$ is located at the 4-position relative to the ring carbon atom bonded to the terminal carbon atom of the olefin and $R^6$ is hydrogen, as in, e.g., 4-chlorophenyl, 4-(trifluoromethoxy)phenyl, 4-(difluoromethoxy)phenyl, 4-isopropylphenyl, 4-tert-butylphenyl, 4-methoxyphenyl, 4-methylphenyl and the like.

For example, the olefinic acid or derivative thereof asymmetrically hydrogenated is
2-(4-difluoromethoxy)phenyl)-3-methyl-2-butenic acid,
2-(4-methylphenyl)-3-methyl-2-butenic acid ethyl 2-(4-(trifluoromethoxy)phenyl)-3-methyl-2-butenate,
2-(4-(tert-butyl)phenyl-3-methyl-2-butenamide, The process is usually conducted under basic conditions. The base can be an alkali metal lower alkoxide of e.g. lithium, sodium or potassium, or hydroxide of e.g. sodium or potassium, or an amine including primary, secondary or tertiary amine such as disopropylamine, ethanolamine, tetramethylenediamine, pyridine, piperidine, morpholine and the like. Preferably the base is a tertiary amine. Any tertiary amine can be used including alkyl, aryl or heterocyclic tertiary amines. Preferably, the tertiary amine is a trialkylamine containing 1 to 4 carbon atoms in each alkyl group, for example: trimethylamine, tri-n-propylamine, and especially triethylamine. When used, the base is present in a molar ratio of base to the substrate of formula I of from about 1:1 to about 1:10 and preferably from about 1:2 to about 1:5. The asymmetric hydrogenation can also be carried out on substrates which are preformed alkali or ammonium salts as well as reaction mixtures comprising acid substrates and the above mentioned bases. When the hydrogenation is carried out using the salt substrates, no additional base is required.

The reaction is preferably conducted in the presence of an inert polar solvent.

Preferably the polar solvent is an alkanol or alkanediol containing up to 10 carbon atoms. It is usually desirable to use an alkanol containing 1 to 3 carbon atoms, such as methanol, ethanol, n-propanol or isopropanol. Methanol is preferred.

The asymmetric hydrogenation reaction is conducted in the presence of a catalyst which is a coordination complex of a metal selected from rhodium, ruthenium or iridium in combination with a chiral metallocenylphosphine or pyrrolidinylphosphine ligand.

The chiral phosphine ligand is usually present in a ratio of from about 0.5 to about 2.0 moles of ligand per mole of metal and preferably in a ratio of from about 1.0 to about 1.2 mole of ligand per mole of metal.

In practice, it is often preferred to have the catalyst in a solid form for the purpose of use, handling and storage. However, the asymmetric hydrogenation is also conveniently carried out in the presence of catalyst formed in situ before or during hydrogenation. Thus for use, the catalyst can be added to the reaction zone usually already containing solvent as a compound per se or in the form of its components which then form the catalyst in situ.

A solid catalyst is prepared by slurrying the organic metal complex in alcohol, such as ethanol, adding about one mole of chiral phosphine ligand per mole of metal in the complex so that a solution is formed, followed by the addition of a suitable anion, such as $PF_6^-$, or other anion which will result in the precipitation or crystallization of a solid, coordination complex either directly from the solvent or upon treatment with an appropriate solvent.

When the catalyst is added as its components, it may be added prior to, during or after the addition of the substrate tetra-substituted olefinic acid or derivative thereof. Components for the preparation of the catalyst in situ are the soluble metal compound, e.g. an organic metal complex with an olefin in which the metal is rhodium, ruthenium or iridium, and the olefin is as described below, and the chiral phosphine and a suitable anion is as discussed below.

The catalyst is added or formed in situ in any effective catalytic amount and usually in the range of from about 0.001 percent to about 5 percent by weight of contained metal based upon the substrate to be hydrogenated.

After addition of the reactants and catalyst and optionally the solvent, hydrogen is added to the mixture until a ratio of from about 2:1 to about 200:1 times the mole quantity of substrate present has been added, preferably the ratio is from about 50:1 to 100:1.

The pressure of the hydrogenation treatment reaction system can vary because the pressure can be usefully varied dependent upon the type of reactant substrate, type of catalyst, size of the hydrogenation apparatus, amount of reactants, amount of catalyst and amount of solvent. Lower pressures, including atmospheric and sub-atmospheric pressures can be used but the pressure is usually a high pressure from about 250 to 900 or even 2000 p.s.i., preferably from about 300 to 700 p.s.i.

Reaction temperatures can be in the range of from about 0° C. to about 110° C.

The completion of the hydrogenation reaction is determined by conventional means and the resulting product is recovered by conventional means such as distillation, filtration, solvent extraction, chromatographic separation and the like.

The coordination complex preferably has the formula $LM(olefin)_2^+ X^-$ wherein L is a chiral metallocenylphosphine ligand or a chiral pyrrolidinyl phosphine ligand, M is rhodium, ruthenium or iridium; the olefin is a mono- or diolefin containing from 2 to 12 carbon atoms and $X^-$ is an anion, such as $ClO_4^-$, $BF_4^-$, $PF_6^-$, or $\beta,\beta$-dimethyl-p-chloro-atropate, $\beta,\beta,$-dimethyl atropate, atropate and the like. Preferably, M is rhodium. Preferably the olefin is a diolefin such as 1,5-cyclooctadiene (COD) or 2,5-norbornadiene (NBD).

For example R is a hydrogen atom, a formyl group, an acyl group such as acetyl, $CF_3CO$, benzoyl, picolinyl, nicotinyl, isonicotinyl, 2-thenoyl, 1-naphthoyl, furoryl, pentafluorobenzoyl, and the like, a hydrocarbyloxycarbonyl group such as tert-butoxycarbonyl, chloesteryloxycarbonyl or the like. A further preferred subclass is when R is tert-butoxycarbonyl or tert-butanoyl. A chiral pyrrolidinylphosphine ligand especially useful in the process of the invention is when R is tert-butoxycarbonyl.

The above chiral pyrrolidinylphosphine ligands and their preparation are generally known in the art. For example, S,S,-BPPM may be prepared via the route shown below.

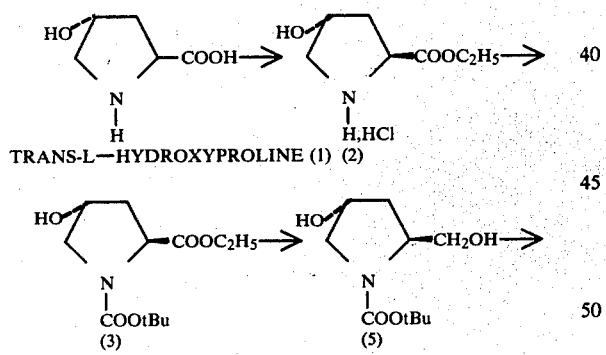

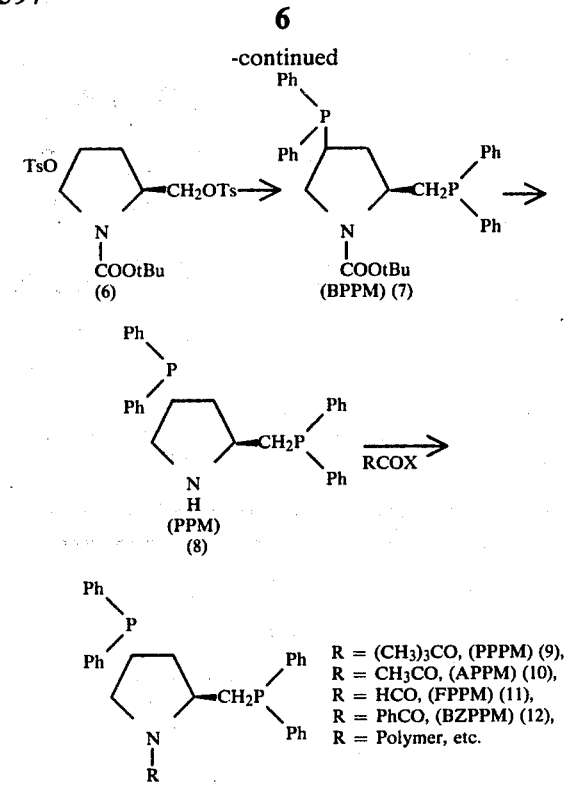

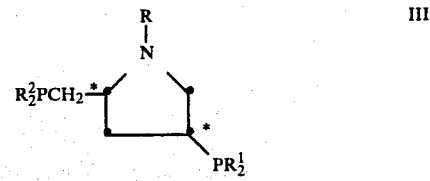

Any chiral pyrrolidinylphosphine ligands may be used. Preferably the chiral pyrrolidinylphosphine ligand has the formula III $$R^2_2PCH_2 \overset{*}{\underset{\underset{\displaystyle PR^1_2}{}}{\overset{\underset{\displaystyle R}{\underset{\displaystyle |}{N}}}{\fbox{\phantom{XXX}}}}}* \qquad III$$

wherein "*" denotes a chiral center; $R^1$ and $R^2$ each independently is a cycloalkyl group, containing 5 to 8 carbon atoms, or an aryl or heteroaromatic group, each containing 5 to 6 ring carbon atoms; and R is a hydrogen atom, a hydrocabyloxycarbonyl group containing 1 to 10 carbon atoms, an acyl group containing from 1 to 10 carbon atoms, a cyano group, an alkyl group, preferably containing 1 to 4 carbon atoms or an aryl group containing 6 to 10 carbon atoms. Preferably, $R^1$ and $R^2$ are phenyl.

For example, R,R-BPPM may be prepared via the two routes shown below using chemical procedures known in the art.

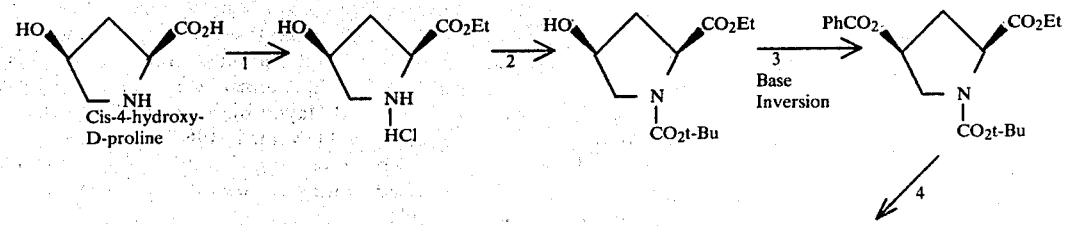

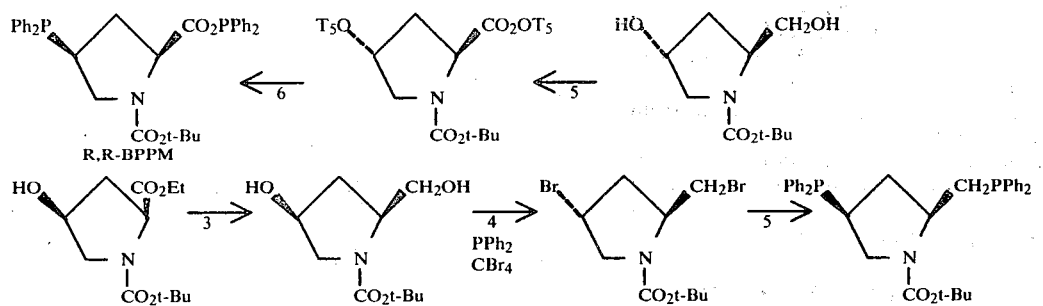

Some common chiral pyrrolidinylphosphine ligands and their abbreviations are set out below in which in formula III R$^1$ and R$^2$ and R$^4$ are phenyl.

| Abbreviation | R is |
| --- | --- |
| PPM | H |
| PPPM | C(O)OC(CH$_3$)$_3$ |
| BPPM | C(O)C(CH$_3$)$_3$ |
| APPM | C(O)CH$_3$ |
| CPPM | CO$_2$cholesteryl |
| FPPM | C(O)H |
| HSPPM | COCH$_2$CH$_2$CO$_2$H |
| MSPPM | COCH$_2$CH$_2$CO$_2$CH$_3$ |
| BZPPM | C(O)C$_6$H$_5$ |
| PCPPM | 2-picolinyl |
| NPPM | 3-picolinyl |
| INPPM | 4-picolinyl |

Any chiral metallocenylphosphine ligand selected from ferrocenyl, ruthenocenyl or osmocenyl groups may be used. Preferably, the chiral metallocenylphosphine ligand is a ferrocenylphosphine ligand and has the formula IV

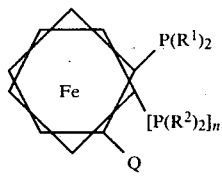

IV wherein substitution by PR$_2^1$ and Q where Q≠PR$_2^1$ results in planar chirality; R$^1$ and R$^2$ each independently is a cycloalkyl group, containing 5 to 8 carbon atoms, or an aryl or heteroatomic group, each containing 5 to 6 ring carbon atoms; Q is an alkyl or alkenyl group containing up to 4 carbon atoms or is CR$^3$R$^4$R$^5$ in which R$^3$ and R$^4$ each independently is a hydrogen atom, an alkyl group, preferably containing 1 to 6 carbon atoms, an aryl containing 6 to 10 carbon atoms, or R$^3$ and R$^4$ together with the carbon atom are a cycloalkyl ring containing 4 to 8 atoms; R$^5$ is a hydrogen atom, a hydroxy group, an acyloxy group containing from 1 to 10 carbon atoms or a group ZR$_2^6$ in which Z is N, P, As or Sb; and R$^6$ is a hydrogen atom, an alkyl group containing 1 to 6 carbon atoms or R$_2^6$ together with the nitrogen atom or phosphorous atom form a heterocyclic ring optionally containing an additional oxygen or nitrogen ring atom and n is 0 or 1. Preferably, Z is N or P.

For example, Q is ethyl, vinyl, 1-(dimethylamino)ethyl, 1-acetoxyethyl, 1-hydroxyethyl, 1-(diethylamino)ethyl, dimethylaminomethyl, 1-(N-morpholinyl)ethyl, 1-(N-piperidinyl)ethyl or 1-(N',N'-dimethyl-N-piperazinyl)ethyl. A further preferred subclass of the invention is when Q is 1-(dimethylamino)ethyl. Another preferred subclass of the invention is when R$^1$ and R$^2$ all are phenyl groups or all are methyl groups. An especially useful subclass is when R$^1$ and R$^2$ both are phenyl groups. Another preferred subclass of the invention is when n is 0.

Some common chiral ferrocenylphosphine ligands and their abbreviations are set out below in which in formula IV R$^1$ and R$^2$ are phenyl.

| | Q is |
| --- | --- |
| n is 0 | |
| PPFA | CH(CH$_3$)N(CH$_3$)$_2$ |
| MPFA | CH(CH$_3$)N(CH$_3$)$_2$ |
| FePN | CH$_2$N(CH$_3$)$_2$ |
| | CH(CH$_3$)N(C$_2$H$_5$) |
| | CH(CH$_3$)—N⟨hexyl⟩ |
| | CH(CH$_3$)—N⟨morpholinyl⟩O |
| | CH(CH$_3$)—N⟨piperazinyl⟩N—CH$_3$ |
| | CH(CH$_3$)OC(O)CH$_3$ |
| EPPF | C$_2$H$_5$ |
| | CH$_2$(CH$_3$)P(CH$_3$)$_2$ |
| n is 1 | |
| BPPFA | CH(CH$_3$)N(CH$_3$)$_2$ |
| BPPFOAC | CH(CH$_3$)OC(O)CH$_3$ |
| BPPFOH | CH(CH$_3$OH |
| BPPEF | C$_2$H$_5$ |
| FeBPN | CH$_2$N(CH$_3$)$_2$ |
| BPPFV | —CH=CH$_2$ |
| BMPFA | CH(CH$_3$)N(CH$_3$)$_2$ (but R$^1$, R$^2$ each is CH$_3$) |
| | CH$_2$(CH$_3$)P(CH$_3$)$_2$ |

The chiral metallocenyl ligands are prepared in the manner in which the ferrocenyl ligands are synthesized as described in the literature, as for example in: Cullen, W. R., et al., *J. Amer. Chem. Soc.*, 102, pages 988–933 (1980) and Haydashi, T. et al., *Bull. Chem. Soc. Japan.*, 53, pages 1138–1151 (1980).

A preferred coordination complex catalyst precursor for generating a catalyst in situ can be one of the formula

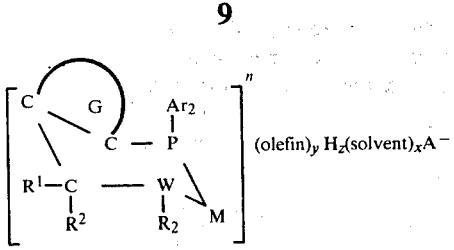

$$\left[ \begin{array}{c} C \overset{G}{\underset{}{\diagdown}} \\ \diagdown C - P \overset{Ar_2}{\underset{}{|}} \\ R^1 - C \underset{|}{\phantom{-}} W \overset{\diagdown}{\underset{R_2}{|}} \\ R^2 \end{array} \right]_n (\text{olefin})_y \, H_z(\text{solvent})_x A^-$$

wherein y=0, 1, or 2; z=2 or 0; G is a chiral metallocenyl group selected from ferrocenyl, ruthenocenyl or osmocenyl or a pyrrolidinyl group; W is N, P, As, or Sb; R is an alkyl group containing 1 to 6 carbon atoms, cycloalkyl containing 4 to 8 carbon atoms, an aryl group containing 6 to 10 carbon atoms; $R^1$ and $R^2$ can be identical or different, and may be a hydrogen atom, an alkyl group or alkoxy group containing 1 to 6 carbon atoms or together $R^1$ and $R^2$ may form a cycloalkyl group containing 4 to 8 carbon atoms; each Ar is an aryl group containing 6 to 10 carbon atoms optionally substituted at the ortho-, meta-, or para-position by a halogen atom, alkyl group or alkoxy group containing 1 to 4 carbon atoms, nitro group, or amine group; M is rhodium, ruthenium or iridium; when y is 2, then the olefin contains from 2 to 12 carbon atoms and when y is 1 then the olefin is a bis-olefin containing from 6 to 10 carbon atoms; H is the hydride ligand which is equal to 0 when y is 1 or 2, or H is equal to 2 when y is 0; $(\text{solvent})_x$ is complexed solvent molecule having a dielectric constant of at least 5 such that $y+z+x=4$; $A^-$ is the anion $ClO_4^-$, $BF_4^-$, $PF_6^-$, atropate anion, $\beta;\beta$-dimethylatropate anion, $\beta,\beta$-dimethyl-p-chloro-atropate anion, and the like; and n=1. For example, W is preferably N or P; Ar is preferably phenyl, the olefin is ethylene, propylene, or preferably 1,5-cyclo-octadiene (1,5-COD), bicyclo-2.2.1-hepta-2,5-diene (i.e., 2,5-norbornadiene, 2,5-NBD) 1,5-hexadiene and the like. Preferably, the olefin is 1,5-COD or 2,5-NBD, M is preferably rhodium, G is preferably a ferrocenyl or pyrrolidinyl derived moiety, each Ar is preferably phenyl, $R^1$ is preferably hydrogen when G is pyrrolidinyl and methyl when A is ferrocenyl; $R^2$ is preferably hydrogen. When G is ferrocenyl, W is preferably N or P and R is methyl, and when G is pyrrolidenyl, then W is preferably P and each R is preferably a phenyl group. Suitable solvents are alkanols, including alkandiols, ethers, aromatic hydrocarbons, sulfolanes and alkylsulfolanes, solvents being but not limited to methanol, tetrahydrofuran, sulfolane, toluene and the like. Preferably the solvent has a dielectric constant of at least 10. Solvents containing strongly-coordinating species ($-CN$, $-PR_2$, $NR_2$) are to be avoided.

Many of the olefinic acid precursors wherein R in formula I can be $-CN$ are disclosed in U.S. Pat. No. 4,132,728 and can be hydroyzed to the acid. All of the olefinic acids and precursors wherein R is $-CN$, $-COOH$ and COOR can be prepared by methods known in the art as, for example, by reaction of an nitrile $R^1-CH_2 CN$ with a ketone of the formula $R^2C(O)R^3$. In some cases, unsaturated nitriles can be converted, if desired to the corresponding unsaturated carboxylic acid or derivative thereof either before hydrogenation or after. Treatment of α- or β-hydroxy acids, e.g. with p-toluene sulfonic acid or $KHSO_4$, yields the unsaturated acids directly. The α- or β-hydroxy acid derivatives can also be converted to their unsaturated counterparts by elimination of water. In another example, a 1-(p-substituted phenyl)-2-methyl-1-propene is brominated, then dehydrobrominated with, e.g., sodium methoxide, and the resulting product is treated with magnesium and carbon dioxide to yield the desired olefinic acid substrate, e.g., 2-(4-substituted phenyl)-3-methyl-2-butenoic acid.

The asymmetric hydrogenation products are useful as biologically active materials or intermediates thereto. For example, some of the compounds, e.g., wherein $R^1$ is a phenyl group, are disclosed as herbicides in, for example, British Pat. No. 1,021,014 and U.S. Pat. No. 4,164,415, while ester derivatives of some of the acids are disclosed as insecticides in, for example, U.S. Pat. Nos. 3,996,244, 4,042,710, 4,199,595; European Pat. No. 6,630, Japanese patent application No. 55/100,338, French Pat. Nos. 919,193, 919,196, and 926,529 and the like.

ILLUSTRATIVE EMBODIMENTS

The following embodiments are presented for the purpose of illustrating the invention only and should not be regarded as limiting the invention in any way. The products were analyzed by combining a fraction thereof with a known amount of benzoic acid marker, subjecting this mixture to esterification with N,O-bis-(trimethylsilyl)acetamide and chromatographing the resulting product. The percent enantiomeric excess (i.e. in the tables) was calculated as the specific rotation of the product times 100 divided by mole fraction of the substrate converted.

EMBODIMENT 1

A 100-ml hydrogenation autoclave was charged with 2.0 mmol of 2-(4-chlorophenyl)-3-methyl-2-butenic acid, 0.005 mmol of $(NBDRhCl)_2$ wherein NBD is 2,5-norbornadiene, 0.0125 mmol of chiral phosphine ligand, 0.01 mmol of $AgBF_4$, 0.05 mmol of triethylamine and 493 mmol of methanol.

The apparatus was purged and pressurized to a hydrogen gauge of 700 p.s.i. After heating the stirred mixture at 80° C. for 4 hours, the autoclave was cooled, vented and solvent removed by rotary evaporation. In many cases crystallization of the isolated product was induced by using a glass rod. Results of the experiments are set forth in Table I below.

TABLE I
ASYMMETRIC HYDROGENATION WITH CHIRAL FERROCENYLPHOSPHINE LIGANDS

| 100-ml autoclave | 2.0 mmol 2-(4-chlorophenyl)- |
| --- | --- |
| 700 psig $H_2$ | 3-methyl-2-butenic acid |
| 4 hours, 80° C. | 0.005 mmol $(NBDRhCl)_2$ |
| | 0.0125 mmol chiral phosphine ligand |
| | 0.01 mmol $AgBF_4$ |
| | 0.05 mmol triethylamine |

| Experiment | Chiral Phosphine Ligand | Conversion (m %) | Selectivity to CPIA[a] | % ee (S/R) |
| --- | --- | --- | --- | --- |
| 1 | R,S—PPFA | 46/51 | >98 | 85 (S) comb[b] |
| 3 | S,R—BPPFA | 99 | >98 | 17 (R) (20)[c] |
| 4 | S,R—PPFP | 99 | >98 | 9.2 (R) |
| 5 | R,S—BPPFOH | 100 | >98 | 8.6 (S) |

[a]CPIA is 2-(4-chlorophenyl)-3-methyl-2-butanoic acid
[b]Comb = Combined yield of two runs.
[c]Confirmed by NMR using chiral shift reagents.

EMBODIMENT 2

Following procedures similar to those described in Embodiment 1, 2-(4-chlorophenyl)-3-methyl-2-butenoic acid was asymmetrically hydrogenated with R,S-PPFA as the chiral phosphine ligand in the presence of various solvents. In each case 75% v/v of the solvent was that indicated under solvent in Table II. The remaining 25% was methanol in which the catalyst had been prepared prior to injection into the system.

TABLE II
ASYMMETRIC HYDROGENATION WITH SOLVENT SERIES

| 100-ml autoclave | 2.0 mmol 2-(4-chlorophenyl)-3-methyl-2-butenic acid |
|---|---|
| 4 hours, 80° C. | 0.005 mmol $(NBDRhCl)_2$ |
| 20 mls solvent | 0.011 mmol R,S—PPFA |
|  | 0.01 mmol $AgBF_4$ |
|  | 0.05 mmol triethylamine |

| Experiment | Solvent (mmol) | Conversion (m %) | Selectivity to CPIA* (gc) | % ee (S/R) |
|---|---|---|---|---|
| 1 | 80:20 v/v ethanol/$H_2O$ | 26 | >98 | 85 (S) |
| 2 | $CF_3CH_2OH$ (194) | 26 | >98 | 73 (S) |
| 3 | methanol[a] (493) | 38 | >98 | 83 (S) |

*CPIA is 2-(4-chlorophenyl)-3-methyl-2-butanoic acid
[a] 300 psig $H_2$

EMBODIMENT 3

Following procedures similar to those described in Embodiment 1 2-(4-chlorophenyl)-3-methyl-2-butenic acid was asymmetrically hydrogenated with R,S-PPFA or SR-PPFA as the chiral ligand (producing S- or R-CPIA respectively) and using various ratios of chiral phosphine ligand to rhodium metal. The rhodium metal source is $(1,5-CODRhCl)_2$ in which COD is cyclooctadiene or $(2,5-NBDRhCl)_2$ in which NBD is norbornadiene. The results of these experiments are set forth in Table III.

TABLE III
ASYMMETRIC HYDROGENTATION WITH VARIED CHIRAL PHOSPHINE LIGAND TO METAL RATIO

| 100-ml autoclave | 0.005 mmol metal complex |
|---|---|
| 700 psig $H_2$ | 0.01 mmol $AgBF_4$ |
| 2.0 mmol 2-(4-chlorophenyl)-3-methyl-2-butenic acid | 0.05 mmol triethylamine |
| $(1,5-CODRhCl)_2$ metal source or | 20 mls methanol (493 mmol) |
| $(2,5-NBDRhCl)_2$ metal source |  |

| Reaction Time (Hour) | Ligand Amount % Relative to Rh | Conversion CPIA = (m %) | Selectivity S—CPIA* (m %) | % ee (S/R) |
|---|---|---|---|---|
| 4 | 110 | 44 | >98 | 76 (R) |
| 8[a] | 110 | 38 | >98 | 83 (R) |
| 4 | 120 | 50 | >98 | 63 (R) |
| 8 | 120 | 62 | >98 | 71 (R) |
| 4 | 130 | 48 | >98 | 72 (S) |
| 8 | 130 | 50 | >98 | 74 (S) |
| 4 | 140 | 51 | >98 | 88 (S) |
| 8 | 140 | 61 | >98 | 77 (S) |
| 4 | 160 | 45 | >98 | 85 (S) |
| 8 | 160 | 55 | >98 | 85 (S) |
| 4 | 200 | 44 | >98 | 83 (S) |
| 8 | 200 | 47 | >98 | 68 (S) |

[a] Run at 300 psig $H_2$
*S—CPIA is S—2-(4-chlorophenyl)-3-methyl-2-butanoic acid

EMBODIMENT 4

A 100-ml hydrogenation autoclave, was charged with 2.0 mmoles of 2-(4-chlorophenyl)-3-methyl-2-butenoic acid, 0.005 mmol of $(2,5-NBDRhCl)_2$, 0.0125 mmol of S,S-BPPM as the chiral phosphine ligand, 0.01 mmol of $BF_4$, 0.05 mmol of triethylamine or potassium hydroxide and 493 mmol of methanol. The apparatus was purged and pressurized to a hydrogen gauge pressure of 700 p.s.i. After heating at room temperature for 17-23 hours, the reaction mixture was treated and the desired product was recovered as described in Embodiment 1. The results of these experiments are set forth in Table IV.

TABLE IV
ASYMMETRIC HYDROGENATION IN THE PRESENCE OF BASE

| 100-ml autoclave | 2.0 mmol substrate: 2-(4-chlorophenyl)-3-methyl-2-butenoic acid |
|---|---|
| 700 psig $H_2$ | |
| 17-23 hrs, room temperature | 0.005 mmol $(NBDRhCl)_2$ |
|  | 0.0125 mmol S,S—$BPPM^2$ |
| 20 mls $CH_3OH$ solvent (493 mmol) | 0.01 $AgBF_4$ |
|  | 0.05 mmol triethylamine or potassium hydroxide |

| Experiment | Comparison Parameters | Substrate Conversion | Selectivity to CPIA* (m %) | % ee (S,R) |
|---|---|---|---|---|
| 1 | triethylamine | 94 | >98 | 82 (R) |
| 2 | potassium hydroxide | 70 | >98 | 87 (R) |

*CPIA is 2-(4-chlorophenyl)-3-methyl-2-butanoic acid

EMBODIMENT 5

Following procedures similar to those described in Embodiment 1, 2-(4-chlorophenyl)-3-methyl-2-butenoic acid was asymmetrically hydrogenated using 0.01 mmol of $[(S,R-PPFA)RhCOD]^+PF_6^-$ as the metal coordination complex. The apparatus was pressurized for 10 hours to a hydrogen gauge pressure of 700 p.s.i. and the temperature was maintained at 80° C. This experiment resulted in a 41 mol percent conversion to 2-(4-chlorophenyl)-3-methyl-2-butanoic acid and an enantiomeric excess of 73% S-2-(4-chlorophenyl)-3-methyl-2-butanoic acid.

EMBODIMENT 6

Following procedures similar to those described in Embodiment 1, 2-(4-chlorophenyl)-3-methyl-2-butenoic acid was asymmetrically hydrogenated using PPFA as the chiral phosphine ligand and $(2,5-NBDRhCl)_2$ as the metal source. In these experiments the rhodium content was held constant while different ratios of substrate, α-isopropenyl-p-chlorophenylacetic acid to rhodium were used. The results of the experiments are set forth in Table V.

TABLE V
ASYMMETRIC HYDROGENATION USING VARIED RHODIUM TO SUBSTRATE RATIOS

| 100-ml autoclave | (R,S)—PPFA amount = 2.1 × metal source amount |
|---|---|
| 700 psig $H_2$, 80° C. | $AgBF_4$ amount = 2 × metal source amount |
| 2.0 mmol substrate: 2-(4-chlorophenyl)-3-methyl-2-butenoic acid | 0.05 mmol triethylamine |
| (2,5-NBD—$RhCl)_2$ metal source with [Rh] held constant | 20 mls methanol (493 mmol) |

| Reaction Time (Hours) | Rh Substrate Ratio | Substrate Conversion (m %) | Selectivity S—CPIA* (m %) | % ee (S/R) |
|---|---|---|---|---|
| 8[a] | 1:100 | 92 | >98 | 76 (S) |
| 4 | 1:100 | 60 | >98 | 78 (S) |
| 8[b] | 1:400 | 23 | >98 | 79 (S) |
| 4 | 1:400 | 17 | >98 | —[c] |
| 8 | 1:200 | 50 | >98 | 63 (R)[d] |

TABLE V-continued

ASYMMETRIC HYDROGENATION USING VARIED RHODIUM TO SUBSTRATE RATIOS

| | | | | |
|---|---|---|---|---|
| 4 | 1:200 | 62 | >98 | 71 (R)[d] |

[a]Used double the solvent amount in this reaction.
[b]4.0 mmol substrate used in this reaction.
[c]ee not determined.
*S—CPIA is 2-(4-chlorophenyl)-3-methyl-2-butanoic acid.
[d]Used (S,R)—PPFA.

EMBODIMENT 7

To a 100-ml hydrogenation autoclave was charged 2.0 mmoles of 2-(4-chlorophenyl)-3-methyl-2-butenoic acid, 0.005 mmol of (1,5-CODRhCl)$_2$ or (2,5-NBDRhCl)$_2$, 0.011 mmol of PPFA as the chiral phosphine ligand, 0.01 mmol of AgBF$_4$, 0.05 mmol of triethylamine and 493 mmol of methanol. The apparatus was purged and pressurized for four hours at 80° C. to a certain hydrogen pressure, which was varied in several different experiments. The results of these experiments are set forth in Table VI.

TABLE VI

ASYMMETRIC HYDROGENATION AT VARIED PRESSURES 100-ml autoclave    0.005 mmol metal complex
2.0 mmol substrate: 2-(4-chloro-    0.011 mmol PPFA ligand (R,S)
phenyl)-3-methyl-2-butenoic acid    0.05 mmol triethylamine
(1,5-CODRhCl)$_2$ metal source or    0.01 mmol AgBF$_4$
(2,5-NBDRhCl)$_2$ metal source    20 ml methanol (493 mmol)
PPFA ligand
4 hours run time, 80° C.

| Experiment | Pressure (psig H$_2$) | Substrate Conversion (m %) | Selectivity CPIA* (m %) | % ee (S/R) |
|---|---|---|---|---|
| 1 | 700 | 52 | >98 | 76 (S) |
| 2 | 700 | 44 | >98 | 76 (R)[b] |
| 3 | 300 | 41 | >98 | —[a] |
| 4 | 100 | 25 | >98 | 88 (S) |
| 5 | 50 | 25 | >98 | 95 (S) |
| 6 | 25 | 15 | >98 | 95 (S) |

*CPIA is 2-(4-chlorophenyl)-3-methyl-2-butanoic acid
[a]ee not determined
[b](S,R)-PPFA used.

EMBODIMENT 8

Following procedures similar to those described in Embodiment 1, 2-(4-chlorophenyl)-3-methyl-2-butenoic acid was asymmetrically hydrogenated using different chiral phosphine ligands in the catalyst system. The results of these experiments are set forth in Table VII below.

TABLE VII

ASYMMETRIC HYDROGENATION WITH VARIED CHIRAL PHOSPHINE LIGANDS 100-ml autoclave    2.0 mmol substrate: 2-(4-chlorophenyl)-
700 psig H$_2$    3-methyl-2-butenoic acid
4 hours, 80° C.    01 mmol catalyst (LRhSx)$^+$BF$_4$$^-$
   in which S is the solvent
20 mls CH$_3$OH solvent    0.0125 mmol chiral phosphine ligand
(493 mmol)    0.05 mmol triethylamine

| Experiment | Ligand | Substrate Conversion (m %) | Selectivity to CPIA* (m %) | % ee (S/R) | Remarks |
|---|---|---|---|---|---|
| 1 | BPPFA | 82 | >98 | 23 (R) | 0.011 mmol ligand |
| 2 | S,R—PPFA | 38 | >98 | 83 (R) | 300 psig |
| 3 | S,S—BPPM | 100 | >98 | 60 (R) | |

*CPIA is 2-(4-chlorophenyl)-3-methyl-2-butanoic acid.

EMBODIMENT 9

Following procedures similar to those described in Embodiments 1 and 7, 2-(4-chlorophenyl)-3-methyl-2-butenoic acid was asymmetrically hydrogenated using BPPM as the chiral phosphine ligand under different pressures. The results of these experiments are set forth in Table VIII below.

TABLE VIII

ASYMMETRIC HYDROGENATION AT VARIED PRESSURE 100-ml autoclave    0.005 mmol metal complex
200 mmol substrate: 2-(4-chloro-    0.011 mmol BPPM ligand
phenyl)-3-methyl-2-butenoic acid    0.05 mmol triethylamine
(2,5-NBDRhCl)$_2$ metal source    0.01 mmol AgBF$_4$
BPPM chiral phosphine ligand    50 mls methanol (493 mmol)
17 hour reaction time, room temp.

| Experiment | Pressure (psig H$_2$) | Substrate Conversion (m %) | Selectivity CPIA* (m %) | % ee (S/R) |
|---|---|---|---|---|
| 1 | 700 | 94 | >98 | 82 (R) |
| 2 | 200 | 90 | >98 | 83 (R) |
| 3 | 50 | 74 | >98 | 85 (R) |

*CPIA is 2-(4-chlorophenyl)-3-methyl-2-butanoic acid

EMBODIMENT 10

Following procedures similar to those described in Embodiments 1 and 5, 2-(4-chlorophenyl)-3-methyl-2-butenoic acid was asymmetrically hydrogenated using BPPFA as the chiral phosphine ligand under different temperature conditions. The results of these experiments are set forth in Table IX.

TABLE IX

ASYMMETRIC HYDROGENATION AT VARIED TEMPERATURES 100-ml autoclave    0.005 mmol metal complex
2.0 mmol substrate: 2-(4-chloro-    0.011 mmol ligand
phenyl)-3-methyl-2-butenoic acid    0.05 mmol triethylamine
(1,5-CODRhCl)$_2$ metal source    0.01 mmol AgBF$_4$
BPPFA ligand    20 mls CH$_3$OH (493 mmol)

| Experiment | Temp (°C.) | Pressure (psig H$_2$) | Substrate Conversion (m %) | Selectivity CPIA* (m %) | % ee (S/R) |
|---|---|---|---|---|---|
| 1 | 40 | 300 | 33 | >98 | 37 (R) |
| 2 | 60 | 300 | 79 | >98 | 33 (R) |
| 3 | 80 | 700 | 99 | >98 | 17 (R) (20)[a] |
| 4 | 60 | 700 | 99 | >98 | 23 (R) |

*CPIA is 2-(4-chlorophenyl)-3-methyl-2-butanoic acid.
[a]Enantiomeric excess determined by NMR spectroscopy and the use of chiral shift reagents.

EMBODIMENT 11

Following procedures similar to those described in Embodiments 1, 5 and 10, 2-(4-chlorophenyl)-3-methyl-2-butenoic acid was asymmetrically hydrogenated using BPPM as the chiral phosphine ligand under different temperature conditions. The results of these experiments are set forth in Table X below.

TABLE X

ASYMMETRIC HYDROGENATION AT VARIED TEMPERATURES 100-ml autoclave    0.005 mmol metal complex
2.0 mmol substrate: 2-(4-chloro-    0.0125 mmol BPPM ligand
phenyl)-3-methyl-2-butenoic acid    0.05 mmol triethylamine
(2,5-NBDRhCl)$_2$ metal source    0.01 mmol AgBF$_4$
700 psig, 4 hours    20 mls methanol (493 mmol)

Substrate Selectivity
Conversion

TABLE X-continued
ASYMMETRIC HYDROGENATION AT VARIED TEMPERATURES

| Experiment | Temp (°C.) | (m %) | CPIA* (m %) | % ee (S/R) |
|---|---|---|---|---|
| 1 | room temp | 39 | >98 | 94 (R) |
| 2 | 40 | 98 | >98 | 76 (R) |
| 3 | 60 | 97 | >98 | 74 (R) |
| 4 | 80 | 96 | >98 | 70 (R) |

≠*CPIA is 2-(4-chlorophenyl)-3-methyl-2-butanoic acid

EMBODIMENT 12

Following procedures similar to those described in Embodiment 1, 2-(4-(difluoromethoxy)phenyl)-3-methyl-2-butenoic acid can be asymmetrically hydrogenated using R,R-BPPM as the chiral phosphine ligand to give 5-2-(4-(difluoromethoxy)phenyl)-3-methyl-2-butanoic acid.

I claim:

1. A process for the asymmetric hydrogenation of a tetra-substituted olefinic acid, which comprises the hydrogenation of a tetra-substituted olefinic acid having formula I

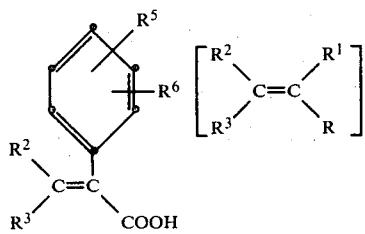

wherein $R^2$ and $R^3$ each is a methyl group or when taken together with the carbon atom to which they are attached form a cyclopropyl group; $R^5$ and $R^6$ each independently is hydrogen, chlorine, fluorine, bromine, or an alkyl or alkoxy group each optionally substituted by one or more halogen atoms in the presence of a coordination complex of rhodium, ruthenium or iridium in combination with a chiral metallocenylphosphine selected from a ferrocenyl-, a ruthenocenyl- or an osmocenylphosphine ligand or pyrrolidinylphosphine ligand.

2. A process according to claim 1 which is conducted in the presence of an inert polar solvent.

3. A process according to claim 2 wherein the inert polar solvent is an alkanol or alkandiol.

4. A process according to claim 3 wherein the solvent is methanol.

5. A process according to claim 1 which is conducted under basic conditions.

6. A process according to claim 5 herein the base is an amine.

7. A process according to claim 6 wherein the amine is trialkylamine.

8. A process according to claim 1 wherein the amine is triethylamine.

9. A process according to claim 1 wherein $R^2$ and $R^3$ each is a methyl group; $R^5$ is hydrogen, chlorine, fluorine, bromine or an alkyl or alkoxy group optionally substituted by one or more chlorine or fluorine atoms and is located at the 4-position relative to the ring carbon atom bonded to the terminal carbon atom of the olefin and $R^6$ is a hydrogen atom.

10. A process according to claim 9 wherein $R^5$ is a chlorine atom, a trifluoromethoxy group, a difluoromethoxy group, an isopropyl group, a tert-butyl group, a methoxy group or a methyl group.

11. A process according to claim 10 wherein the tetra-substituted olefinic acid or derivative thereof is 2-(4-chlorophenyl)-3-methyl-2-butenoic acid.

12. A process according to claim 1 wherein the coordination complex has the formula $LM(olefin)_2+X^-$ wherein L is a chiral metallocenylphosphine ligand or a chiral pyrrolidinylphosphine ligand; M is rhodium, ruthenium or iridium, the olefin is a mono- or diolefin containing from 2 to 12 carbon atoms and $X^-$ is an anion.

13. A process according to claim 12 wherein L is a chiral ferrocenylphosphine ligand or a chiral pyrrolidinylphosphine ligand; M is rhodium; the olefin is a diolefin selected from 1,5-cyclooctadiene and 1,3-norbornadiene and $X^-$ is $ClO_4^-$, $BF_4^-$, or $PF_6^-$.

14. A process according to claim 13 wherein the chiral ligand is a pyrrolidinylphosphine ligand of the formula

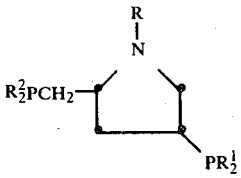

wherein $R^1$ and $R^2$ each independently is a cycloalkyl group, containing 5 to 8 carbon atoms, or an aryl or heteroaromatic group each containing 5 or 6 ring carbon atoms; and R is a hydrogen atom, a hydrocarbyloxycarbonyl group containing 1 to 10 carbon atoms; an acyl group, containing from 1 to 10 carbon atoms, a cyano group, an alkyl group containing 1 to 6 carbon atoms or an aryl group containing 6 to 10 carbon atoms.

15. A process according to claim 14 wherein in the chiral pyrrolidinylphosphine ligand $R^1$ and $R^2$ each is a phenyl group; and R is a hydrogen atom, a hydrocarbyloxycarbonyl group containing 1 to 10 carbon atoms, or an acyl group containing from 1 to 7 carbon atoms optionally substituted by carboxy or carboxyalkyl.

16. A process according to claim 15 wherein in the chiral pyrrolidinylphosphine ligand R is a hydrogen atom, a formyl group, acetyl, tert-butanoyl, $CF_3CO$, benzoyl, picolinyl, nicotinyl, isonicotinyl, 2-thenoyl, 1-naphthoyl, furoryl, pentafluorobenzoyl, tert-butoxycarbonyl or chloesteryloxycarbonyl.

17. A process according to claim 16 wherein R is tert-butoxycarbonyl or tert-butanoyl.

18. A process according to claim 13 wherein the chiral ligand is a ferrocenylphosphine ligand of the formula

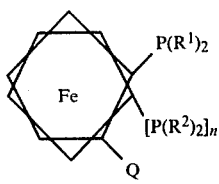

$R^1$ and $R^2$ each independently is a cycloalkyl group containing 5 to 8 carbon atoms or an aryl or heteroaromatic group each containing 5 or 6 ring carbon atoms; Q is an alkyl or alkenyl group containing up to 4 carbon atoms or is $CR^3R^4R^5$ in which $R^3$ and $R^4$ each independently is a hydrogen atom, an alkyl group containing 1 to 6 carbon atoms or an aryl group containing 6 to 10 carbon atoms, or $R^3$ and $R^4$ together with the carbon atom to which they are attached is a cycloalkyl group containing 4 to 8 carbon atoms, $R^5$ is a hydrogen atom, a hydroxy group, an acyloxy group or a group $ZR_2^6$ or $PR^6R^7$ in which Z is N, P, As or Sb and $R^6$ is a hydrogen atom, an alkyl group containing 1 to 6 carbon atoms or $R_2^6$ together with the nitrogen atom or phosphorus atom form a heterocyclic ring optionally containing an addition oxygen or nitrogen ring atom and n is 0 or 1.

19. A process according to claim 18 wherein in the chiral ferrocenylphosphine ligand $R^1$ and $R^2$ are all phenyl groups and Q is an ethyl, vinyl, 1-(dimethylamino)ethyl, 1-acetoxyethyl, 1-hydroxyethyl, 1-(diethylamino)ethyl, dimethylaminomethyl, 1-(N-morpholinyl)ethyl, 1-(N-piperazinyl)ethyl or 1-(N',N'-dimethyl-N-pierazinyl)ethyl group.

20. A process according to claim 19 wherein Q is 1-(dimethylamino)ethyl and n is 0.

21. A process according to claim 12 wherein the coordination complex catalyst has the formula

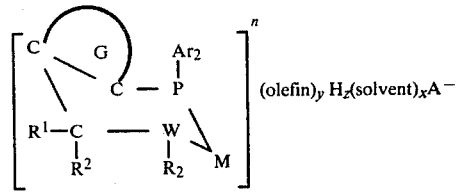

wherein y=0, 1, or 2; z=2, or 0; G is a chiral metallocenyl group selected from ferrocenyl, ruthenocenyl or osmocenyl or a pyrrolidinyl group; W is N, P, As, or Sb; R is an alkyl group containing 1 to 6 carbon atoms, cycloalkyl containing 4 to 8 carbon atoms, an aryl group containing 6 to 10 carbon atoms; $R^1$ and $R^2$ can be identical or different, and may be a hydrogen atom, an alkyl group or alkoxy group containing 1 to 6 carbon atoms or together $R^1$ and $R^2$ may form a cycloalkyl group containing 4 to 8 carbon atoms; each Ar is an aryl group containing 6 to 10 carbon atoms optionally substituted at the ortho-, meta-, or para-position by a halogen atom, alkyl group or alkoxy group containing 1 to 4 carbon atoms, nitro-group, or amine group, M is rhodium, ruthenium or iridium; when y is 2, then the olefin contains from 2 to 12 carbon atoms and when y is 1, then the olefin is a bis-olefin containing from 6 to 10 carbon atoms; H is the hydride ligand which is equal to 0 when y is 1 or 2, or H is equal to 2 when y is 0, (solvent)$_x$ is complexed solvent molecule having a dielectric constant of at least 5 such that y+z+x=4; $A^-$ is the anion $ClO_4^-$, $BF_4^-$, $PF_6^-$, atropate anion, $\beta X^-$, $\beta$-dimethylatropate anion, $\beta,\beta$-dimethyl-p-chloro-atropate anion, and n=1.

22. A process according to claim 21 wherein in the coordination complex catalyst G is a ferrocenyl or pyrrolidinyl group, $R^1$ is a hydrogen atom; $R^2$ is a methyl group; each Ar is a phenyl group; each R is a methyl group; when G is ferrocenyl then W is N and when G is pyrrolidenyl then W is P; the olefin is 1,5-cyclooctadiene or 2,5-norbornadine; M is rhodium, n is 1 and the solvent has a dielectric constant of at least 10.

23. A process according to claim 1 conducted in methanol in the presence of triethylamine and a coordination complex of the formula LM(olefin($_2$+$X^-$ wherein L is a chiral ferrocenylphosphine ligand or a chiral pyrrolidinylphosphine ligand; M is rhodium; the olefin is 1,5-cyclooctadiene or 1,3-norbornadiene and $X^-$ is $ClO_4^-$, $BR_4^-$ or $PF_6^-$.

24. A process according to claim 23 wherein the tetra-substituted olefinic acid or derivative thereof is a 2-(4-chlorophenyl)-3-methyl-2-butenoic acid.

* * * * *